United States Patent
Andrews et al.

(10) Patent No.: US 6,958,337 B2
(45) Date of Patent: *Oct. 25, 2005

(54) CRYSTALLINE ANTIFUNGAL POLYMORPH

(75) Inventors: David R. Andrews, Maplewood, NJ (US); William Leong, Westfield, NJ (US); Anantha Sudhakar, East Brunswisk, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/786,886

(22) Filed: Feb. 25, 2004

(65) Prior Publication Data

US 2004/0204423 A1 Oct. 14, 2004

Related U.S. Application Data

(63) Continuation of application No. 09/166,445, filed on Oct. 5, 1998, now Pat. No. 6,713,481.
(60) Provisional application No. 60/061,231, filed on Oct. 7, 1997.

(51) Int. Cl.[7] .................... A61K 31/496; C07D 405/14
(52) U.S. Cl. ................... 514/254.07; 544/366
(58) Field of Search ....................... 544/366; 514/254.07

(56) References Cited

U.S. PATENT DOCUMENTS 6,713,481 B1 * 3/2004 Andrews et al. ....... 514/254.07

* cited by examiner

Primary Examiner—Emily Bernhardt
(74) Attorney, Agent, or Firm—Gerard E. Reinhardt

(57) ABSTRACT

The crystalline polymorph Form I of (−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one represented by the formula I

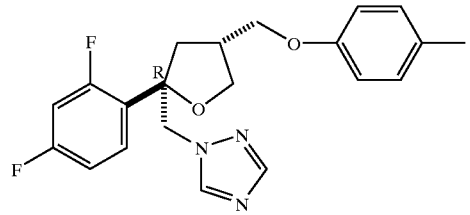

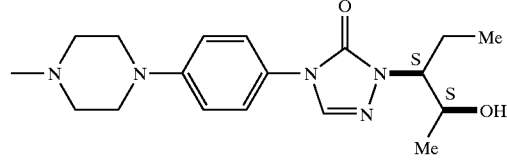

pharmaceutical compositions containing such a polymorph and methods of using such a polymorph to treat fungal infections in mammals are disclosed.

7 Claims, 10 Drawing Sheets

CRYSTALLINE ANTIFUNGAL POLYMORPH

CROSS-REFERENCE TO RELATED APPLICATIONS

This application is a continuation application of U.S. patent application Ser. No. 09/166,445, filed, Oct. 5, 1998, now U.S. Pat. No. 6,713,481, which claims the benefit under 35 U.S.C. §119(e) of U.S. provisional application Ser. No. 60/061,231, filed Oct. 7, 1997.

BACKGROUND OF THE INVENTION

This invention relates to the most stable crystalline polymorph Form I of (−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one represented by the formula I (hereinafter "the compound of formula I")

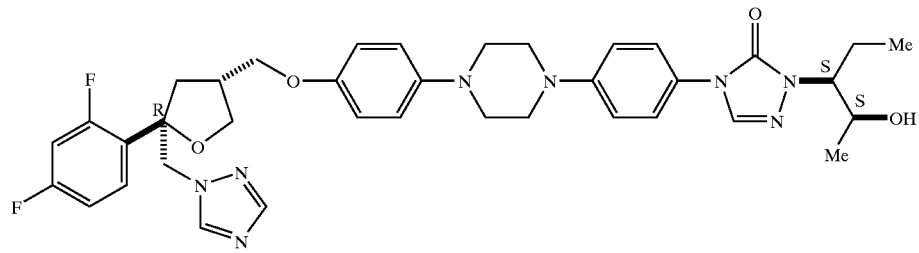

pharmaceutical compositions containing such polymorph and methods of using such polymorph to treat fungal infections in mammals.

International Publication Numbers WO/95/17407 (published 29 Jun. 1995 and WO 96/38443(published 5 Dec. 1996) disclose methods of making the compound of formula I and using it to treat antifungal infections in mammals. These International Patent Publications do not disclose or refer to, or even suggest the possible existence of a crystalline polymorph of the compound of formula I; the synthetic procedures disclosed therein produce the compound of formula I as an amorphous solid.

To prepare pharmaceutical compositions containing the compound of formula I for administration to mammals in accordance with exacting health registration requirements of the U.S. and international health registration authorities, e.g. the FDA's Good Manufacturing Practices("GMP") requirements, there is a need to produce the compound of formula I in as pure a form as possible, especially a form having constant physical properties.

SUMMARY OF THE INVENTION

We have discovered that the compound of formula I can exist in the form of three crystalline polymorphs, each having distinctly different from each other and from the amorphous form in their physico-chemical data, their physical properties and their methods of preparation. These three novel crystalline polymorph forms described in this specification are hereinafter referreds to as form I, form II and Form III. Of the three forms. Form I is the most stable.

Accordingly, this invention provides a crystalline polymorph Form I of (−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one represented by formula I

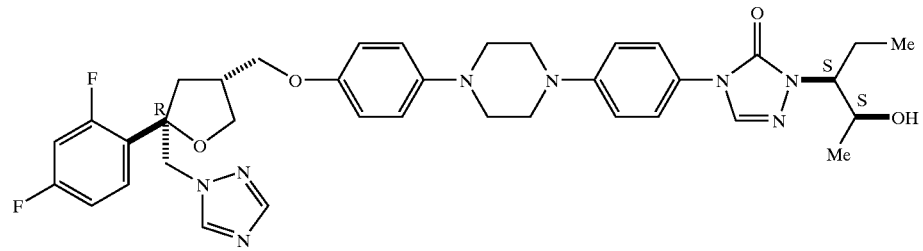

and characterized by the following x-ray powder diffraction pattern expressed in terms of "d" spacing and relative intensities("RI"):

| d spacing (±0.04) | RI |
|---|---|
| 6.10 | Medium |
| 4.63 | Medium |
| 4.10 | Wide |

-continued

| d spacing (±0.04) | RI |
|---|---|
| 3.69 | Wide |
| 3.05 | Wide |

This invention also provides a crystalline polymorph Form I of(−)-4-[4-[4-[4-[[(2R-cis)-5-(2,4-difluorophenyl) tetrahydro-5-(1H-1,2,4-triazol-1-ylmethyl)furan-3-yl] methoxy]phenyl]-1-piperazinyl]phenyl-2,4-dihydro-2-[(S)-1-ethyl-2(S)-hydroxylpropyl]-3H-1,2,4-triazol-3-one characterized by the following x-ray powder diffraction pattern (Table 1) expressed in terms of "d" spacings and relative intensities ("RI")(S=strong, M=medium, W=weak, V=very, D=diffuse and VWD, for example=very weak diffuse):

TABLE 1

| d spacing | relative intensity |
|---|---|
| 22.14 | VWD |
| 12.27 | VWD |
| 11.37 | M |
| 10.35 | VWD |
| 8.85 | M |
| 7.90 | VWD |
| 7.52 | W |
| 6.77 | W |
| 6.10 | M |
| 5.82 | M |
| 5.63 | M |
| 5.52 | M |
| 5.41 | M |
| 5.17 | W |
| 4.95 | VS |
| 4.84 | M |
| 4.63 | M |
| 4.54 | M |
| 4.42 | S |
| 4.29 | VWD |
| 4.23 | WD |
| 4.10 | W |
| 4.02 | WD |
| 3.98 | M |
| 3.86 | W |
| 3.82 | W |
| 3.76 | W |
| 3.69 | W |
| 3.63 | W |
| 3.47 | M |
| 3.45 | WD |
| 3.36 | W |
| 3.30 | VW |
| 3.24 | VWD |
| 3.21 | WD |
| 3.17 | VWD |
| 3.14 | VWD |
| 3.05 | W |
| 2.99 | VWD |
| 2.95 | VWD |
| 2.90 | VWD |
| 2.87 | VWD |
| 2.84 | VWD |
| 2.77 | VWD |
| 2.72 | WD |
| 2.67 | VWD |
| 2.65 | VWD |
| 2.61 | VWD |
| 2.58 | VWD |
| 2.52 | VWD |
| 2.48 | VWD |
| 2.44 | VWD |
| 2.41 | VWD |
| 2.35 | VWD |

TABLE 1-continued

| d spacing | relative intensity |
|---|---|
| 2.34 | VWD |
| 2.28 | VWD |
| 2.26 | VWD |

This invention further provides pharmaceutical composition containing the crystalline polymorph of Forms I, and methods of treating and/or preventing fungal infections using such a crystalline polymorph.

DETAILED DESCRIPTION OF THE INVENTION

The crystalline polymorph Form I of(−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl] phenyl-2,4-dihydro-2-[(S)-1-ethyl-2(S)-hydroxylpropyl]-

3H-1,2,4-triazol-3-one provides an antifungal drug having the following advantages compared to its amorphous form in the priorr art: lower impurity content and more consistent product quality i.e., more consistent physical characteristics including more consistent color, rate of dissolution and ease of handling; as well as a longer term stability.

Figure 2:
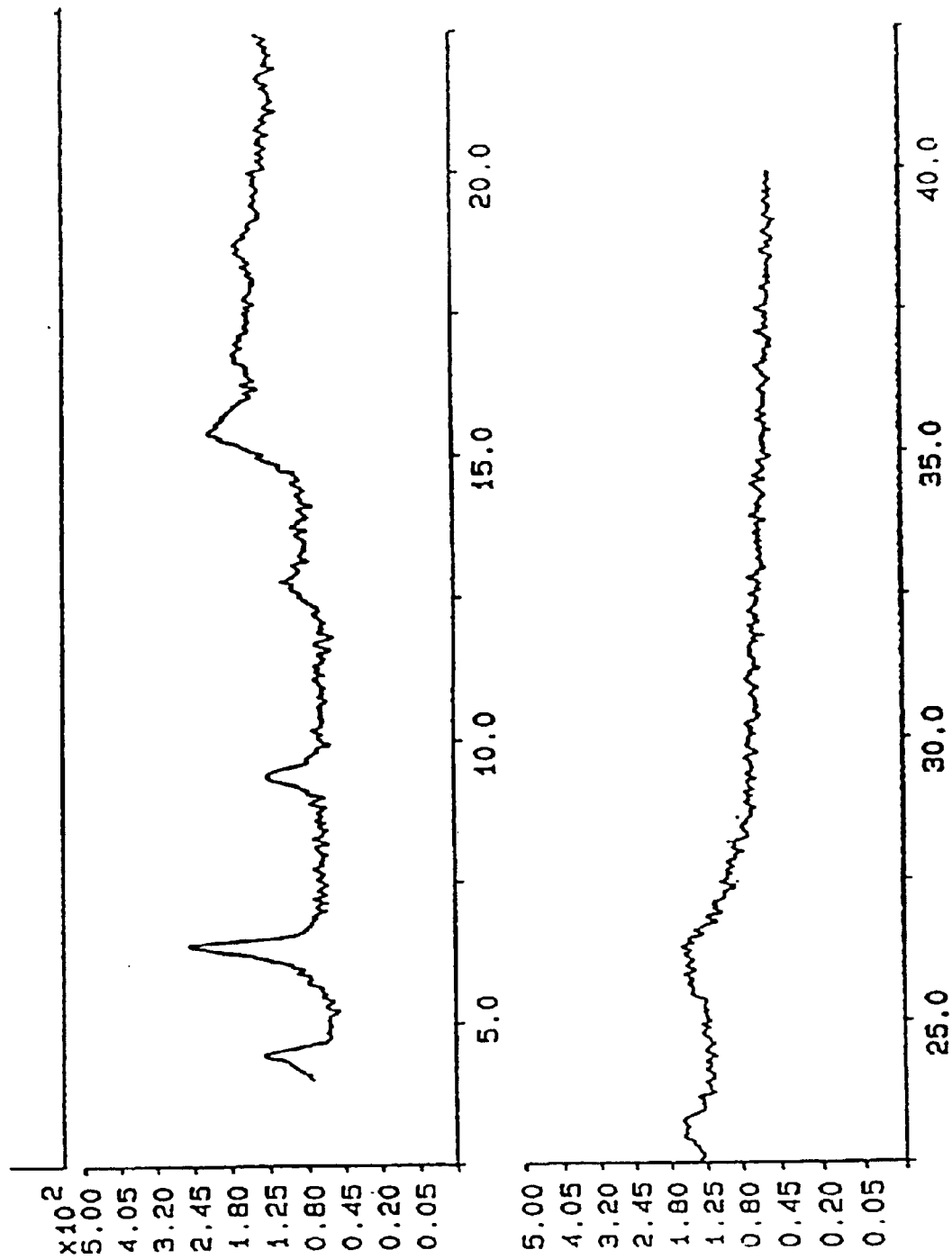
FIG. 2 presents a characteristic x-ray powder diffraction pattern of the polymorph of form II [Vertical Axis: Intensity (CPS, counts (square root)); Horizontal Axis: Two Theta (degrees)]; x-ray diffraction indicates form II is partially amorphous.
Figure 3:
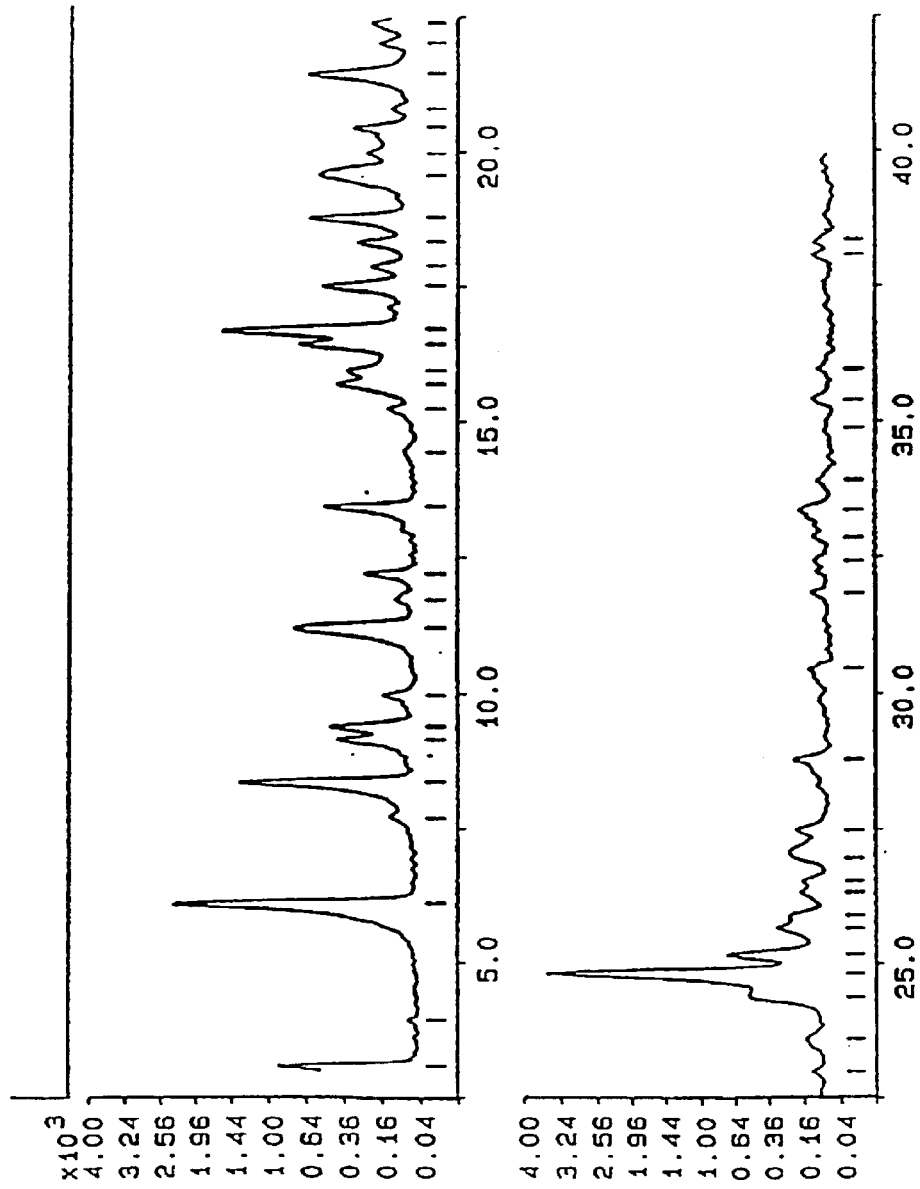
FIG. 3 presents a characteristic x-ray powder diffraction pattern of the cyrstalline polymorph of form III [Vertical Axis: Intensity, (CPS, counts (square root)); Horizontal Axis: Two Theta(degrees)]
Figure 4:
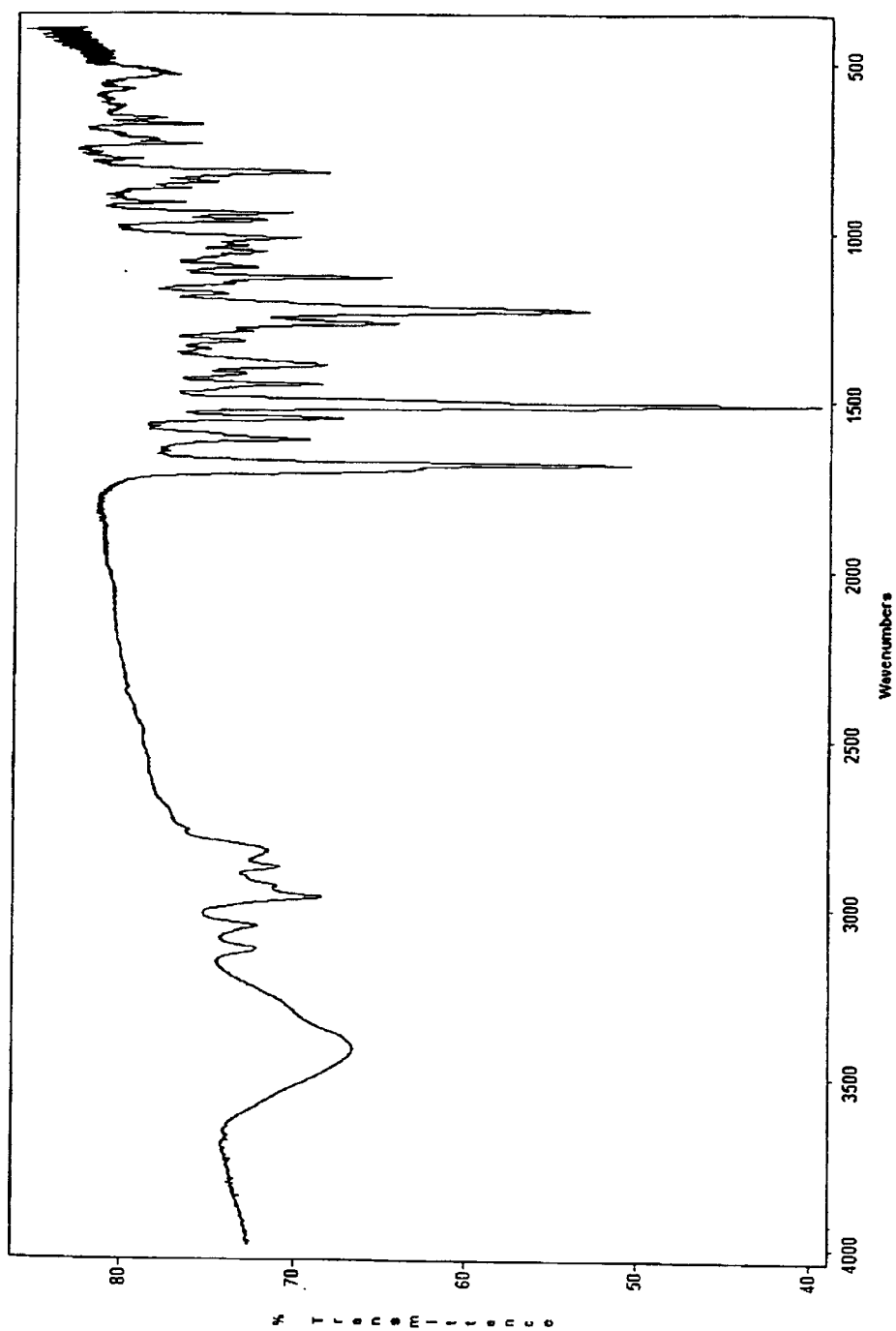
FIG. 4 presents a characteristic infrared spectrum of the crystalline polymorph of form I in a potassium bromide pellet[Vertical Axis; Transmittance(Percent); Horizontal Axis: wavenumber $(cm^{-1})$].
Figure 5:
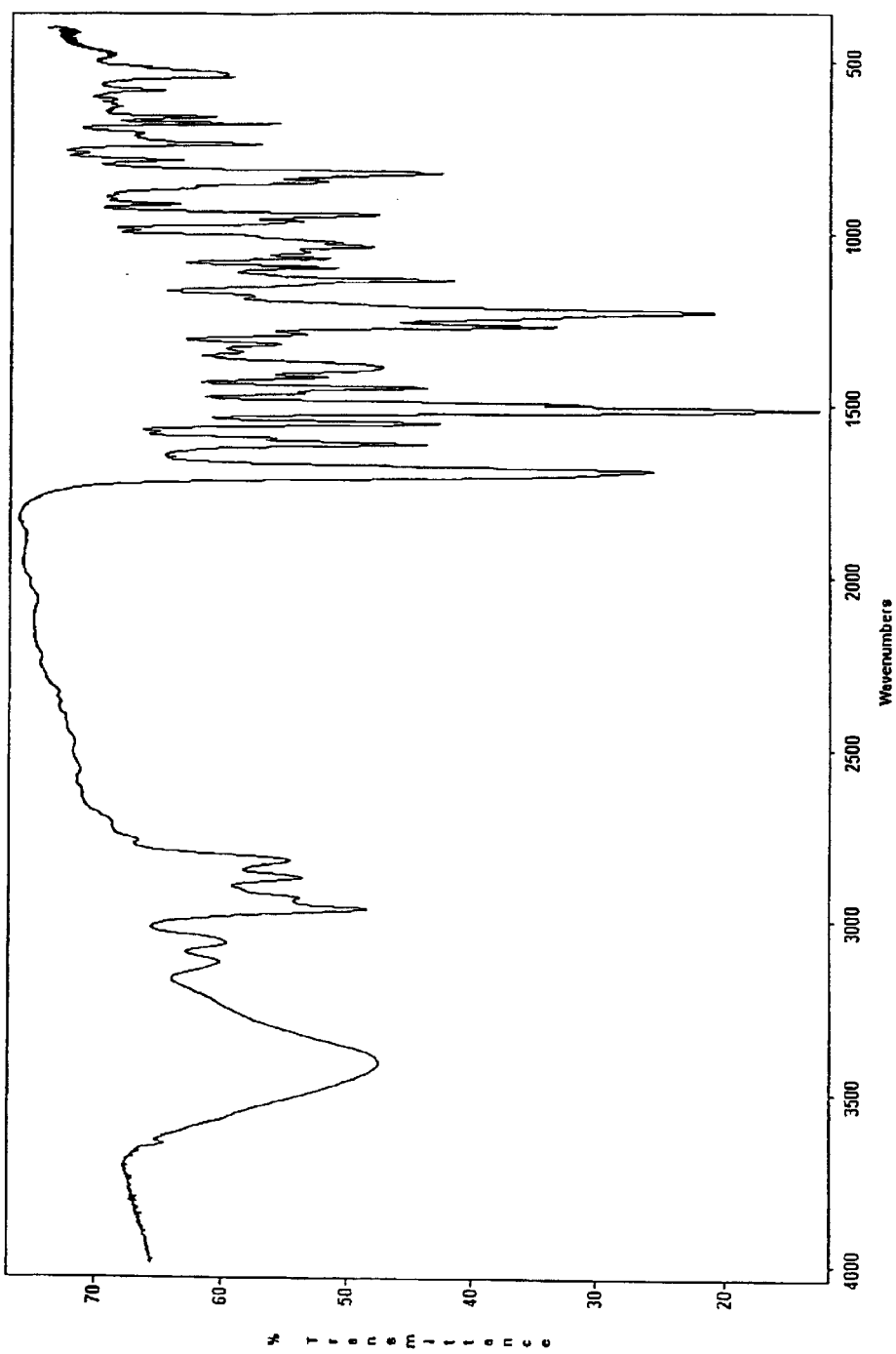
FIG. 5 presents a characteristic infrared spectrum of the crystalline polymorph of form II in a potassium bromide pellet[Vertical Axis; Transmittance(Percent); Horizontal Axis: wavenumber $(cm^{-1})$].
Figure 6:
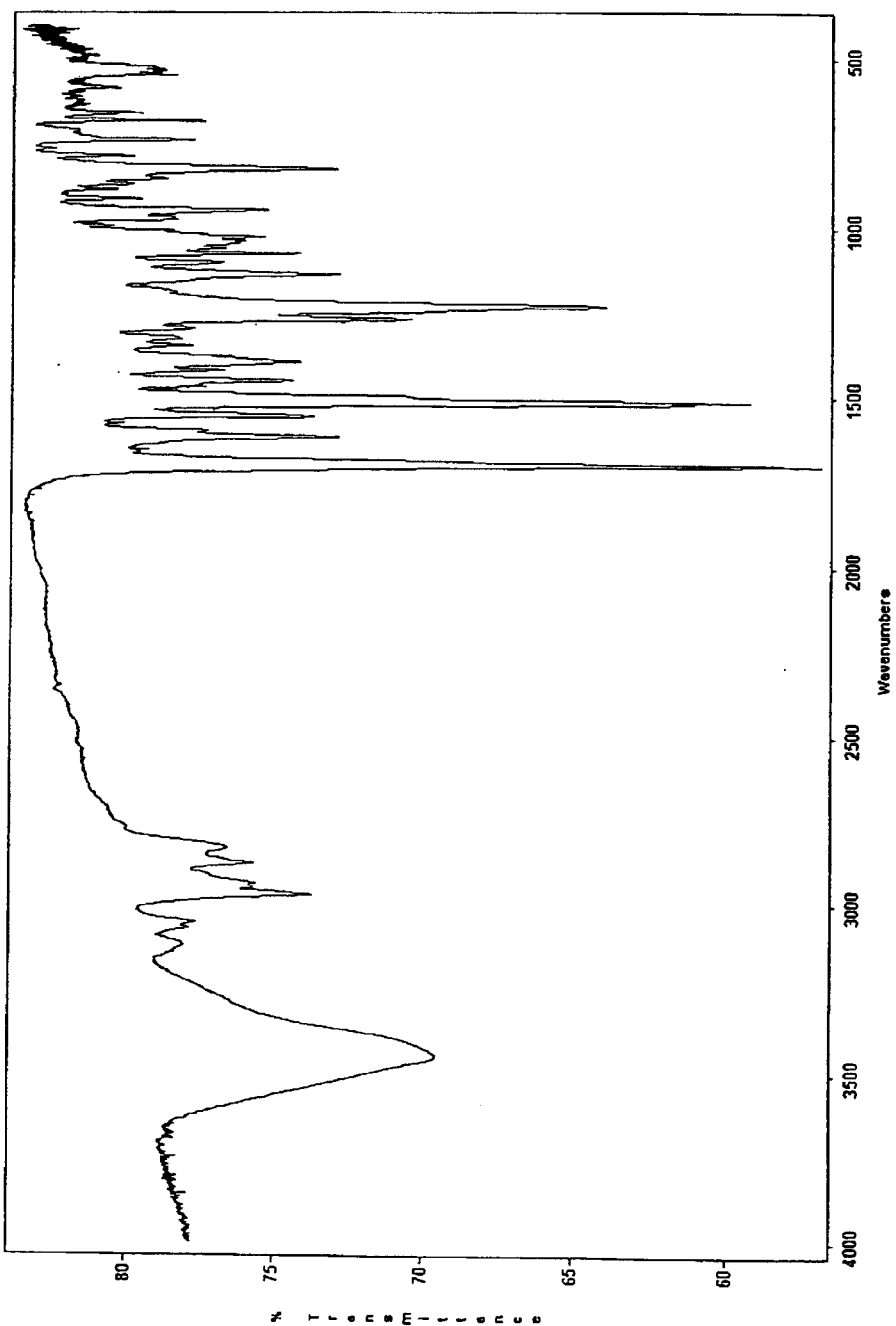
FIG. 6 presents a characteristic infrared spectrum of the crystalline polymorph of form III in a potassium bromide pellet[Vertical Axis; Transmittance(Percent); Horizontal Axis: wavenumber $(cm^{-1})$].
Figure 7:
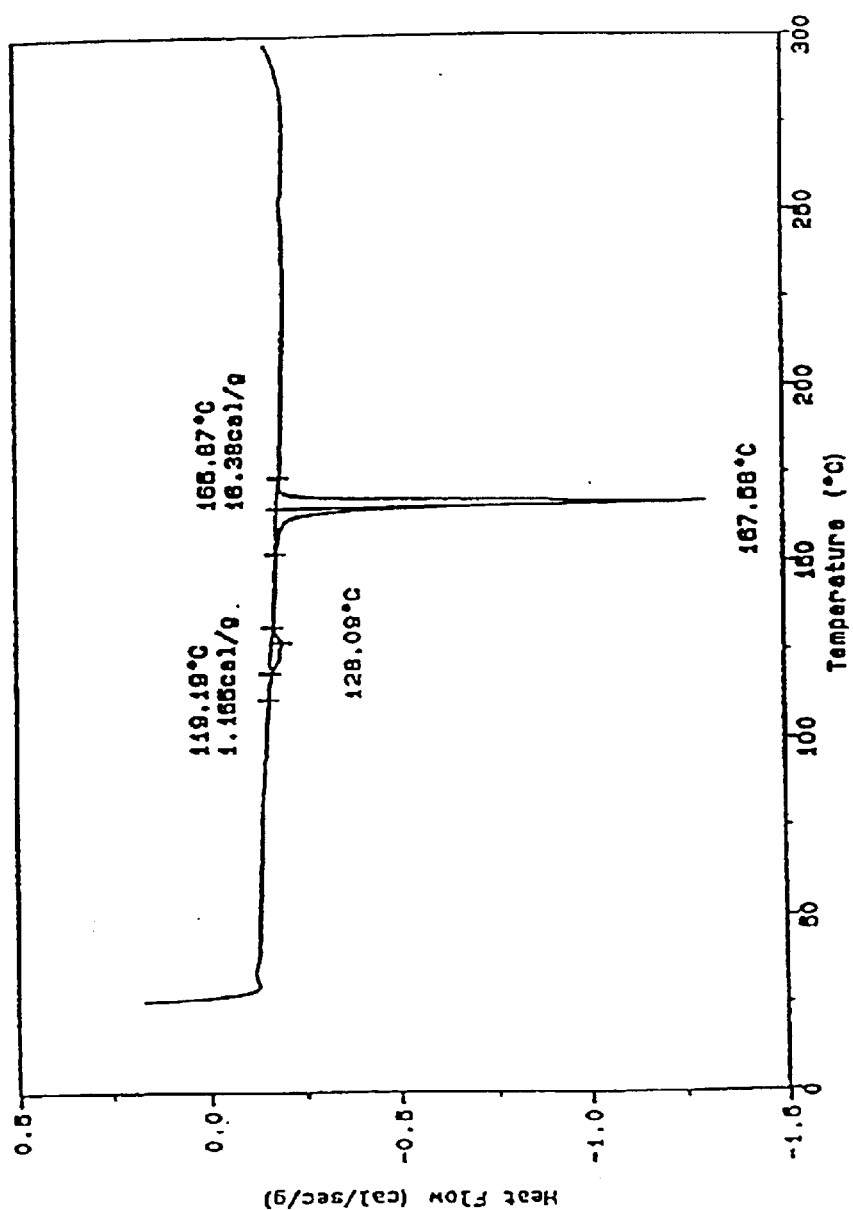
FIG. 7 presents a characteristic differential scanning calorimetry thermogram of the crystalline polymorph of form I [taken on a DuPont 2100: Thermal Analysis under a nitrogen atmosphere; 10° C./min scan rate; single endotherm, onset temperature: about 166° C.; Vertical Axis; Heat Flow in cal/sec/g; about 166° Horizontal Axis: Temperature in degrees centigrade].
Figure 8:
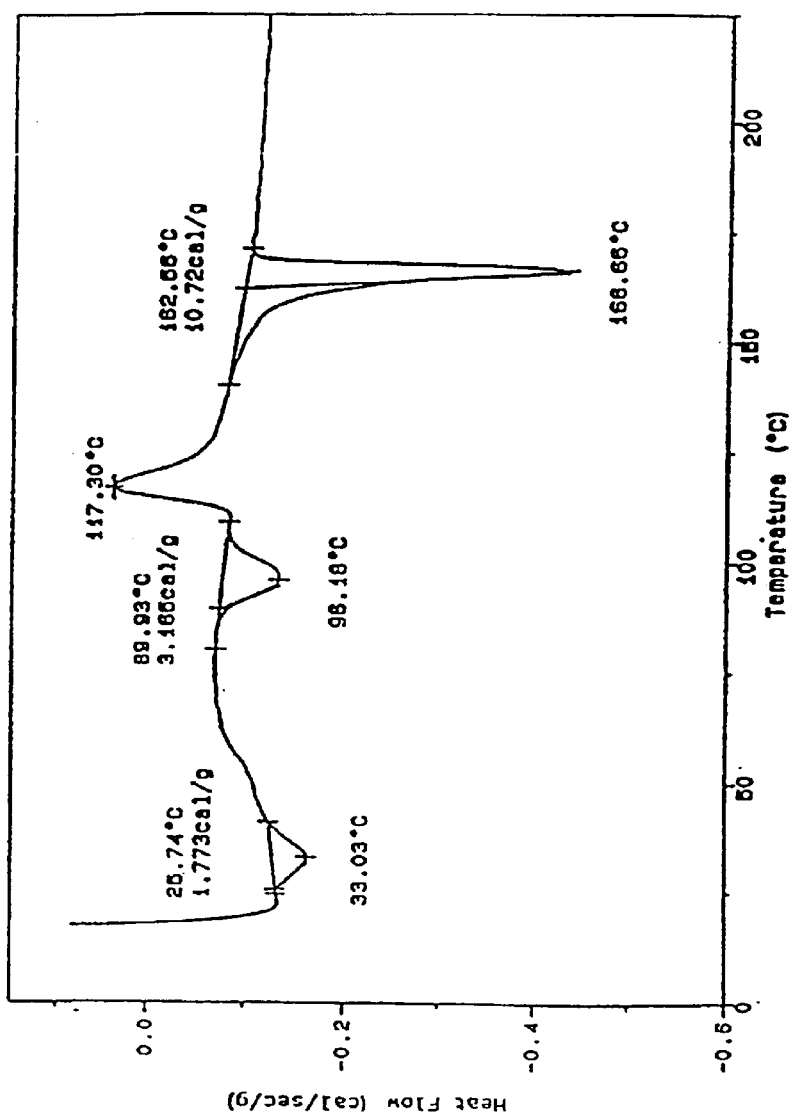
FIG. 8 presents a characteristic differential scanning calorimetry thermogram of the crystalline polymorph of form II [taken on a DuPont 2100: Thermal Analysis under a nitrogen atmosphere; 10° C./min scan rate; endotherm, onset temperature about 26° C.; endotherm, onset temperature about 90° C.; exotherm, start temperature about 113° C.; endotherm onset temperature about 163° C.; Vertical Axis; Heat Flow in cal/sec/g; Horizontal Axis: Temperature in degrees centigrade]
Figure 9:
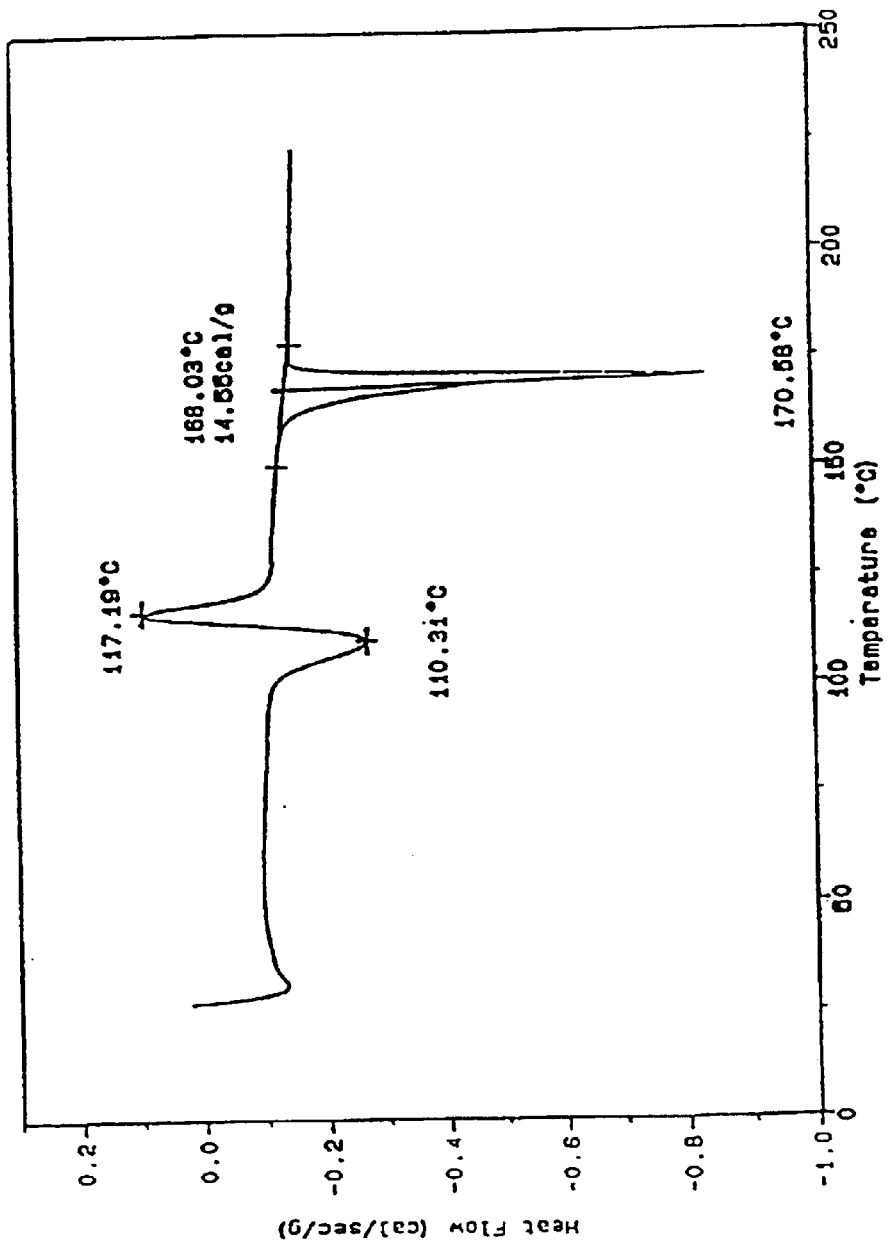
FIG. 9 presents a characteristic differential scanning calorimetry thermogram of the crystalline polymorph of form III [taken on a DuPont 2100: Thermal Analysis under a nitrogen atmosphere; 10° C./min scan rate; endotherm, onset temperature about 98° C.; exotherm, start temperature about 114° C.; endotherm, onset temperature about 168° C.; Vertical Axis; Heat Flow in cal/sec/g; Horizontal Axis: Temperature in degrees centigrade]

The three crystalline polymorphic forms of the compound of formula designated as Form 1, II and III can readily be distinguished from one another by examination of the characteristic x-ray Diffraction patterns (see FIGS. 1–3), the characteristic infrared spectra (see FIGS. 4–6) and the characteristic Differential Scanning Calorimetry (DSL) thermograms (FIGS. 7–9). Form 1, the most stable form, did not convert into any other form under normal storage conditions (15°–30° C. and protected from light) or under the following stress conditions:

150° C. for 2 hours

75° C. for 6 weeks

97% relative humidity at ambient temperature for 2 minutes

75% relative humidity at 40° C. for 6 weeks

The DSC thermograms shown in FIGS. 8 and 9 indicate that Form II and Form III thermally convert into the more stable Form I at temperatures between 100 and 125° C. The characteristic physico-chemical data of crystalline polymorph Form I of the compound of Formula I are summarized in the following Table.

TABLE

Figure 1:
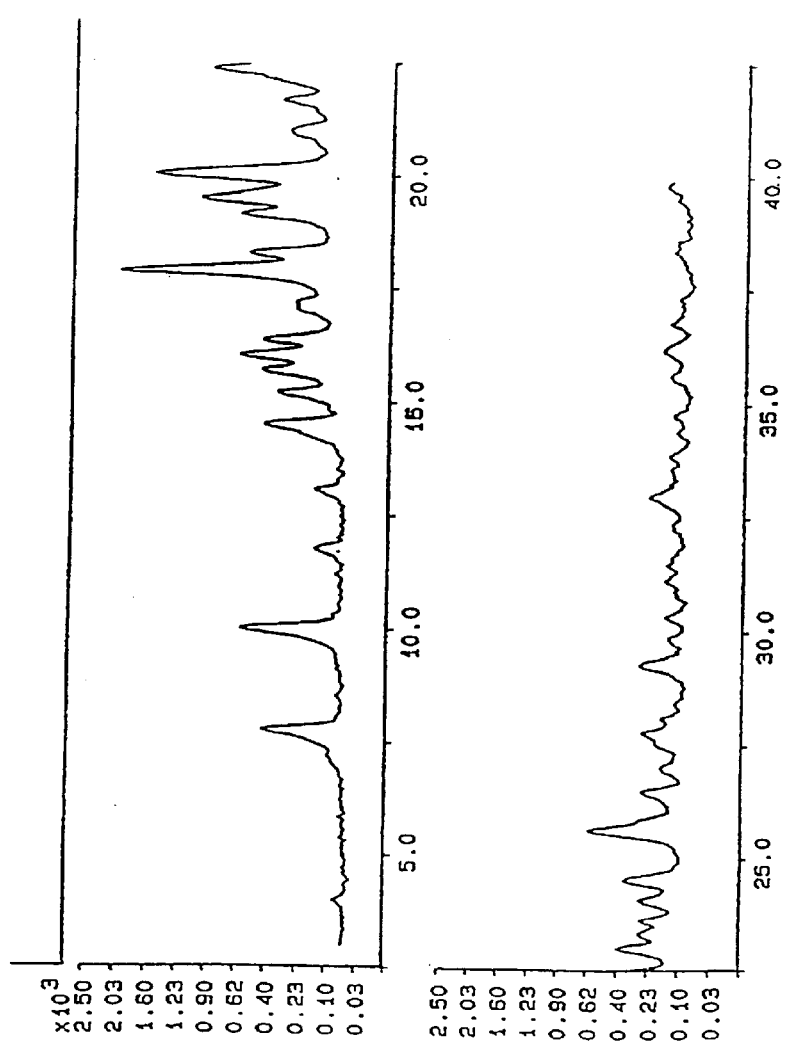
FIG. 1 presents a characteristic x-ray powder diffraction pattern of the cyrstalline polymorph of form I [Vertical Axis: Intensity (CPS, counts (square root)); Horizontal Axis: Two Theta(degrees)].
Figure 10:
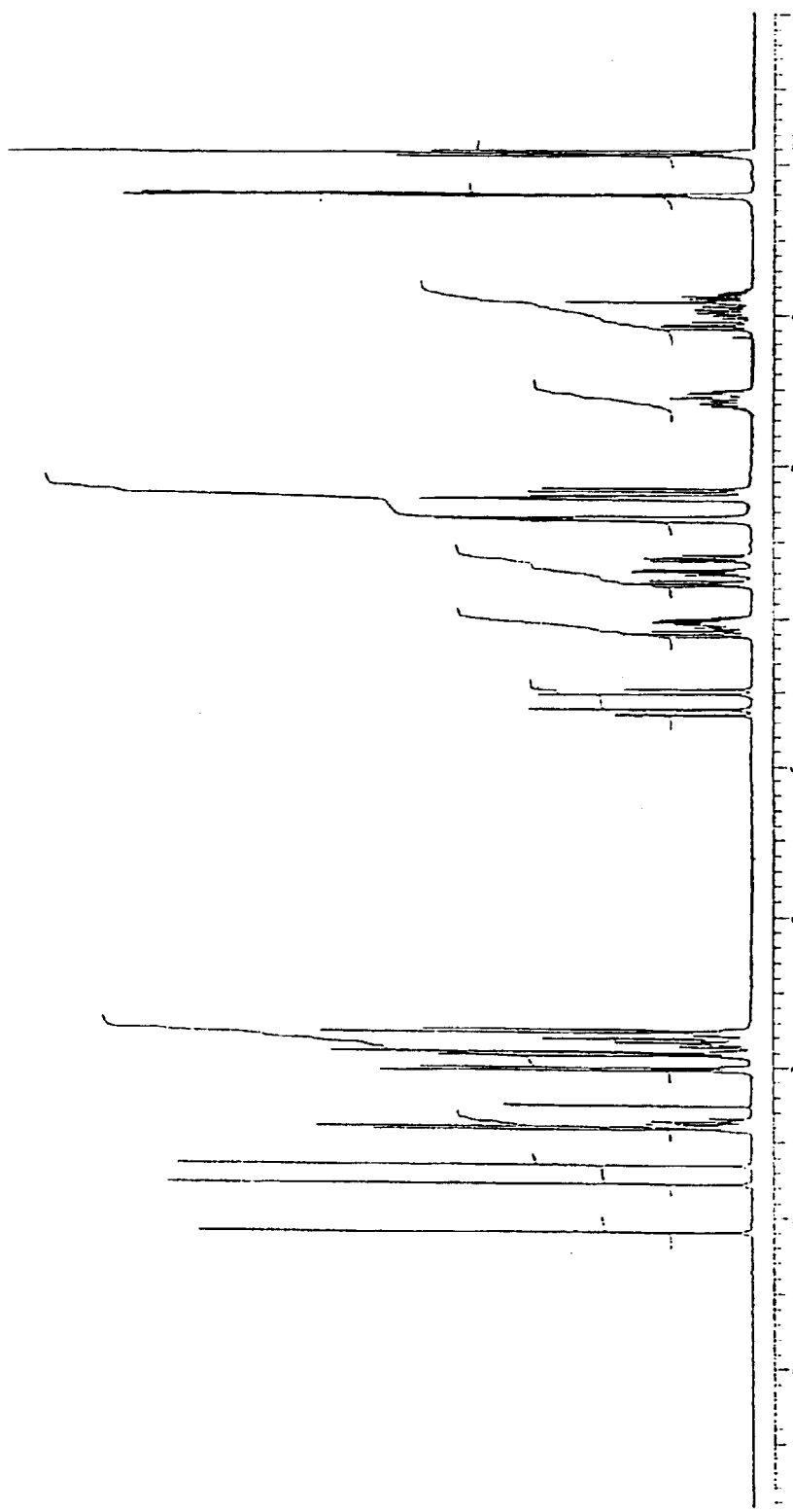
FIG. 10 presents a characteristic $^1$H nmr spectrum of the crystalline polymorph of formsI, II and III[taken on a Vvarian XL400 in $CDCl_3$ at 400 MHz with TMS as an internal standard].

| Characteristic Physico-Chemical Data of Crystalline Polymorph Form I of the Compound of Formula I | |
|---|---|
| Melting Point Range: | 164–165° C.[1] |
| Physical Appearance: | white to off-white powder |
| Specific Rotation: | $[a]^{25}D = -29.4$[2] |
| X-ray Powder Diffraction Pattern: | See FIG. 1 and Table 1 |
| Differential Scanning Calorimetry Thermogram | FIG. 7 |
| Proton NMR Spectrum | FIG. 10 |

[1]USP Class Ia procedure used to determine melting point range.
[2]Concentration: 10 mg/mL in methanol.

All of these advantages inherent in the crystalline polymorph Form I of the compound of this invention would be useful in the development and approval of a pharmaceutical product containing the antifungal drug of formula I.

The crystalline polymorphic form of the compound of Form I may be formed by crystallizing the compound of formula I (as the free base) using a solvent system such as acetonitrile, methanol in combination with water in a v/v ratio of 1.5:1 to 1:1.5, preferably about 1:1; and isopropyl alcohol in combination with water in a volume/volume (v/v) ratio of 1.5:1 to 1:1.5, preferably about 1:1. The solvent or solvent system were typically healed to reflux and slowly cooled to 60–40° C. with agitation and thereafter cooled slowly to room temperature (20°–25° C.) or even 0° (with acetonitrile) with continued agitation for ½ to 1 hour. The crystalline polymorphic form of the compound of form II may be formed by crystallizing the compound of formula I (as the free base) using a solvent system such as acetone-water in a volume/volume (v/v) ratio of 1.5:1 to 1:1.5, preferably about 1:1., or methylene chloride. The Form III product obtained from methylene chloride also contained some amorphous form. The solvent or solvent system were typically healed to reflux and slowly cooled without agitation to room temperature (20°–25° C.) The crystalline polymorphic form of the compound of form III may be formed by adding the compound of formula I (as the free base) to a solvent system such as boiling methanol and allowing the resulting solution to cool without agitation to room temperature.

The infrared spectrum of the crystalline polymorph of form I taken in the form of a potassium bromide pellet is characterized by the following peaks:

| frequency (cm$^{-1}$) |
|---|
| 3118 cm-1 |
| 3055 |
| 2967 |
| 2935 |
| 2876 |
| 2830 |
| 1700 |
| 1687 |
| 1616 |
| 1551 |
| 1511 |
| 1451 |
| 1394 |
| 1272 |
| 1234 |
| 1136 |
| 1017 |
| 964 |
| 943 |
| 824 |
| 737 |
| 681 |
| 664 |

The complete infrared spectrum of the crystalline polymorph of form II taken in the form of a potassium bromide pellet is characterized by the following peaks:

| frequency (cm$^{-1}$) |
|---|
| 3121 cm-1 |
| 3066 |
| 2969 |
| 2934 |
| 2874 |
| 2827 |
| 1691 |
| 1616 |
| 1598 |
| 1554 |
| 1512 |
| 1501 |
| 1452 |
| 1420 |
| 1394 |
| 1328 |
| 1297 |
| 1272 |
| 1230 |
| 1186 |
| 1137 |
| 1101 |
| 1075 |
| 1056 |
| 1039 |
| 1027 |
| 965 |
| 943 |
| 915 |
| 849 |
| 824 |
| 786 |
| 738 |
| 680 |
| 660 |
| 584 |
| 545 |
| 537 |

The complete infrared spectrum of the crystalline polymorph of form III taken in the form of a potassium bromide pellet is characterized by the following peaks:

| frequency (cm$^{-1}$) |
|---|
| 3120 cm−1 |
| 3072 |
| 3054 |
| 2971 |
| 2939 |
| 2874 |
| 2832 |
| 1699 |
| 1616 |
| 1598 |
| 1557 |
| 1512 |
| 1396 |
| 1271 |
| 1231 |
| 1136 |
| 1101 |
| 1075 |
| 1027 |
| 953 |
| 913 |
| 824 |
| 787 |
| 737 |
| 682 |
| 659 |

The infrared spectra were obtained on a Mattson Galaxy 6021 FTIR spectrometer. The potassium bromide pellets were prepared in accordance with the USP procedure <197K>, U.S. Pharmacopeia, National Formulary, USP XXIII, NF XVIII.

The x-ray powder diffraction patterns were measured on a Philips ADP3720 automated diffractometer system (model PW 1800). The radiation source was copper (K-alpha) and the long fine focus tube connected to a Philips XRG 3100 x-ray generator at 45 KV and 40 mA. The take-off angle was 6 degrees and a graphite monochromator as used. A scintillation detector was employed and data was acquired with a scan rate of 0.025 degrees per second, a step size of 0.010 and a step time of 40 seconds per degree.

The x-ray powder diffraction pattern distinctive for polymorph form 1 descarbonylethoxyloratadine expressed in terms of the following distinctive "d" spacing and relative intensties("RI") is provided hereinbelow:

| d spacing (±0.04) | RI |
|---|---|
| 6.10 | Medium |
| 4.63 | Medium |
| 4.10 | Wide |
| 3.69 | Wide |
| 3.05 | Wide |

A more complete x-ray powder diffraction pattern for the crystalline polymorph of the compound of formula I expressed in "d" spacings and relative intensities ("RI") with V, M, W, V, and D defined as herein above is provided hereinbelow in Table 1:

TABLE 1

| d spacing | relative intensity |
|---|---|
| 22.14 | VWD |
| 12.27 | VWD |
| 11.37 | M |
| 10.35 | VWD |
| 8.85 | M |
| 7.90 | VWD |
| 7.52 | W |
| 6.77 | W |
| 6.10 | M |
| 5.82 | M |
| 5.63 | M |
| 5.52 | M |
| 5.41 | M |
| 5.17 | W |
| 4.95 | VS |
| 4.84 | M |
| 4.63 | M |
| 4.54 | M |
| 4.42 | S |
| 4.29 | VWD |
| 4.23 | WD |
| 4.10 | W |
| 4.02 | WD |
| 3.98 | M |
| 3.86 | W |
| 3.82 | W |
| 3.76 | W |
| 3.69 | W |
| 3.63 | W |
| 3.47 | M |
| 3.45 | WD |
| 3.36 | W |
| 3.30 | VW |
| 3.24 | VWD |
| 3.21 | WD |
| 3.17 | VWD |
| 3.14 | VWD |
| 3.05 | W |
| 2.99 | VWD |
| 2.95 | VWD |
| 2.90 | VWD |
| 2.87 | VWD |
| 2.84 | VWD |
| 2.77 | VWD |
| 2.72 | WD |
| 2.67 | VWD |
| 2.65 | VWD |
| 2.61 | VWD |
| 2.58 | VWD |
| 2.52 | VWD |
| 2.48 | VWD |
| 2.44 | VWD |
| 2.41 | VWD |
| 2.35 | VWD |
| 2.34 | VWD |
| 2.28 | VWD |
| 2.26 | VWD |

The crystalline polymorph Form II of(−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one is characterized by the following x-ray powder diffraction pattern expressed in terms of "d" spacing and relative intensities ("RI"):

| d spacing (±0.04) | RI |
|---|---|
| 20.05 | Medium |
| 13.84 | Strong |

The crystalline polymorph Form II of(−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one is characterized by the following x-ray powder diffraction pattern expressed in terms of "d" spacings and relative intensities ("RI")(S=strong, M=medium, W=weak, V=very D=diffuse and VWD, for example=very weak diffuse):

| d spacing | relative intensity |
|---|---|
| 20.05 | M |
| 13.84 | S |
| 9.44 | M |
| 6.90 | VWD |
| 5.75 | WD |
| 5.28 | VWD |
| 4.75 | VWD |
| 3.85 | VWD |
| 3.43 | VWD |

The crystalline polymorph Form III of(−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one is characterized by the following x-ray powder diffraction pattern expressed in terms of "d" spacing and relative intensities ("RI"):

| d spacing (±0.04) | RI |
|---|---|
| 28.69 | Strong |
| 14.45 | Strong |
| 10.59 | Strong |
| 7.27 | Wide |
| 6.59 | Wide |
| 4.14 | Medium |
| 3.58 | Very Strong |
| 3.53 | Medium |

The crystalline polymorph form III of(−)-4-[4-[4-[4-[[(2R-cis)-5-(2,4-difluorophenyl)tetrahydro-5-(1H-1,2,4-triazol-1-ylmethyl)furan-3-yl]methoxy]phenyl]-1-piperazinyl]phenyl-2,4-dihydro-2-[(S)-1-ethyl-2(S)-hydroxylpropyl]-3H-1,2,4-triazol-3-one is characterized by the following x-ray powder diffraction pattern expressed in terms of "d" spacings and relative intensities ("RI")(S=strong, M=medium, W=weak, V=very D=diffuse and VWD, for example=very weak diffuse):

| d spacing | relative intensity |
|---|---|
| 28.69 | S |
| 22.51 | VWD |
| 14.45 | S |
| 11.44 | VW |
| 10.59 | S |
| 9.65 | W |
| 9.41 | W |
| 8.88 | W |
| 7.90 | M |
| 7.54 | VW |
| 7.27 | W |
| 6.82 | VWD |
| 6.59 | W |
| 6.13 | VWD |
| 5.82 | W |
| 5.64 | W |
| 5.57 | W |
| 5.39 | M |
| 5.29 | S |
| 5.17 | VWD |
| 5.05 | W |
| 4.94 | W |
| 4.84 | W |
| 4.72 | M |
| 4.52 | W |
| 4.45 | VW |
| 4.38 | VWD |
| 4.34 | V |
| 4.28 | VW |
| 4.14 | M |
| 4.03 | W |
| 3.97 | W |
| 3.87 | VW |
| 3.77 | VWD |
| 3.66 | WD |
| 3.58 | VS |
| 3.53 | M |
| 3.47 | WD |
| 3.44 | WD |
| 3.39 | WD |
| 3.36 | WD |
| 3.29 | W |
| 3.25 | W |
| 3.15 | VWD |
| 3.12 | VWD |
| 3.10 | WD |
| 2.99 | VWD |
| 2.94 | VWD |
| 2.85 | WD |
| 2.81 | WD |
| 2.78 | WD |
| 2.76 | WD |
| 2.72 | VWD |
| 2.71 | VWD |
| 2.69 | VWD |
| 2.64 | VWD |
| 2.58 | VWD |
| 2.53 | WD |
| 2.50 | VWD |
| 2.42 | VWD |
| 2.40 | VWD |
| 2.36 | WD |
| 2.35 | WD |
| 2.32 | VWD |
| 2.26 | VWD |

Pharmaceutical Compositions

Pharmaceutical compositions of this invention may contain in addition to an anti-fungally effective amount of crystalline polymorph of the compound of formula I as the active ingredient, inert pharma-ceutically acceptable carriers that may be solids or liquids. Solid form compositions include powders, tablets, dispersible granules, capsules, cachets, and suppositories. A solid carrier can be one or more substances which may also act as diluants, flavoring agents, solubilizers, lubricants, suspending agents, binders or tablet disintegration agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5 to about 20 percent of the active ingredient. Suitable solid carriers are magnesium carbonate, magnesium stearate, talc, sugar, lactose, pectin, dextrin, starch, gelatin, tragacanth, methycelulose, sodium carboxymethyl-cellulose, a low melting wax. cocoa butter and the like. The term "compositions" is intended to include the formulation of the active compound with encapsulating material as carrier providing a capsule in which the active component (with or without other carriers) is surrounded by carrier, which is thus in association with it. Similarly, caches are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for topical administration. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can e made by dispersing the finely divided active component in water with viscous material, i.e., natural or synthetic gums, resins, methylcellulose, sodium carboxymethylcellulose and other well-known suspending agents.

Topical formulation useful for nasal or ophthalmic administration are also contemplated. Topical formulation suitable for nasal administration may be solutions or suspensions. Ophthalmic formulations may be solutions, suspension or ointments. Ointments usually contain lipophilic carriers such as mineral oil and/or petrolatum. Solution for ophthalmic administration may contain sodium chloride, acid and/or base to adjust the pH as well as purified water and preservatives, which normally contains a non-toxic, pharmaceutically acceptable topical carrier may be applied daily to the affected skin until the condition has improved.

The anti-fungally effective amount of the crystalline polymorph of the compound of formula I for topical administration varies from 0.1 to 20% by weight of the total pharmaceutical composition, which normally contains one or more non-toxic, pharmaceutically acceptable topical carriers; the pharmaceutical composition may be applied daily to the affected area of the skin until the fungal infection has been irradiated The preferred amount varies from 0.5 to 10% by weight of the total pharmaceutical composition.

The anti-fungally effective amount of the crystalline polymorph of the compound of formula I for oral administration varies from about 1 to 30 mg/day, more preferably about 1 to 20 mg/day and most preferably about 1 to 10 mg/day in single or divided doses.

Parenteral forms to be injected intravenously, intramuscularly, or subcutaneously are usually in the form of a sterile soluon, and may contain salts or glucose to make the solution isotonic.

In general, the parenteral dosage for humans for antifungal use ranges from abou.25 mg per kilogram of body weight per day to about 20 mg kilogram of body weight per day being preferred.

The exact amount, frequency and period of administration of the compound of the present invention for antifungal use will vary, of course, depending upon the sex, age and medical condition of the patent as well as the severity of the antifungal infection as determined by the attending clinician.

General Experimental

The compounds of this invention are prepared in accordance with the following Examples using commercially available starting materials.

In solution, no crystalline form exists, and thus the physiochemical solution characteristics, i.e. $^1$H nmr spectra, ultraviolet spectra and specific rotations of the crystalline polymorph and amorphous forms of the compound of formula I are the same. The $^1$H nmr shown in FIG. 10 is consistent with the structure of the compound of formula I. The specific rotation as measured at the D line of sodium at 25° C. is −29.4.

EXAMPLE 1A

Preparation of Crystalline Polymorph Form I of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one One hundred and sixty four grams of the crude product produced in accordance with Example 32 of International Patent Publication No. WO 95/17407 published 29 Jun. 1995 was dissolved in refluxing methanol (1.64L). The hot solution was filtered through a pad of celite, and warmed back to reflux. To the solution was added water (984 ml) while maintaining a reflux temperature. The solution was allowed to cool slowly to about 45° C. The resulting mixture was agitated for 1 hour at this temperature, then cooled slowly to room temperature and further agitated for 1 hour. The solids that formed were collected by filtration and washed with chilled methanol-water (1:1, about 524 ml). The product was then dried in an oven (45° C., 29 psi vacuum, 24 hours) to yield 156.5 g of white crystals.

EXAMPLE 1B

Preparation of Crystalline Polymorph Form I of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Add 95 Kg of the crude product produced in accordance with Example 32 of International Patent Publication No. WO 95/17407 published 29 Jun. 1995 and 885 L (9×) of methanol to a first reaction vessel blanketed with nitrogen.

Heat the mixture with agitation to reflux (a temperature of 60–65° C.)

Maintain stirred mixture at reflux for 30 minutes or until solution is achieved

Pump the hot solution through an in-line tither (normally 0.22 micron) to a second reaction vessel.

Add 95 L (1×) methanol to first vessel.

Heat, with agitation, the methanol in the first reaction vessel to reflux and pump hot methanol solution through the in-line filter into the second reaction vessel.

Heat so formed solution in the second reaction vessel to a reflux temperature of 60–65° C.

Slowly add 570 L (6×) of purified water USP through in-line filter into the second reaction vessel while maintaining the solution in the second vessel at reflux (temperature should rise to 77° C.

Cool slowly the so-formed solution in the second reaction vessel over about a 30 minute period to 70° C.

Stir the so-formed mixture at 70° C. to effect crystallization and to form a slurry.

Cool the so-form slurry slowly over a period of at least 1 hour to about 40° to 45° C.

Stir the resulting slurry at a temperature of about 40° C. to 45° C. for at least 30 minutes Cool the so-formed slurry slowly over a period of at least 1 hour to room temperature (15–25° C.)

Continue stirring the so-formed slurry at a temperature of 15° to 25° C. for a period of about 2 hours.

Filter the slurry from the second reaction vessel into a centifuge (in two batches). Centrifuge to separate the solvent and remove solvent.

Add 380 L (4×) of purified water USP and 380 L (4×) methanol to the first reaction vessel. Stir the so-formed solution and adjust the temperature to 15–25° C.

Wash each of the two batches with the chilled methanol/water solution delivered through the in-line filter from the first reactor and centrifuge.

Remove the solvent mixture from the centrifuges.

Transfer the two batches of solid from the centrifuges and place them on trays.

Dry the solid in an air draft oven at a dryer temperature of 35° to 45° C. for about 14 hours or until the loss on drying is ≦0.2% by weight.

EXAMPLE 2

Preparation of Crystalline Polymorph Form I of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Two grams (2 g) of crude the starting material prepared in accordance with Example 1 was dissolved in refluxing isopropyl alcohol (20 mL). To the solution was added water (20 ml) while maintaining a reflux temperature. The solution was allowed to cool slowly to about 63° C. when crystallization occurred. The resulting mixture was agitated for 10 mins at this temperature, then cooled slowly to room temperature and further agitated for 1 hour. The solids that formed were collected by filtration. The product was then dried in a draft oven (45° C., 24 hours) to yield a white solid.

EXAMPLE 3

Preparation of Crystalline Polymorph Form I of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Five grams (5 g) of the crude starting material prepared in accordance with Example 1 was dissolved in refluxing acetonitrile (100 mL). The solution was allowed to cool slowly to about 50° C. when crystallization occurred. The resulting mixture was agitated for 30 mins at this temperature, then cooled slowly to 0° C. and further agitated for 30 mins. The solids that formed were collected by filtration and washed with chilled acetonitrile (25 mL). The product was then dried in an oven (40° C., 29 psi vacuum, 12 hours) to yield 3.9 g of white crystals.

EXAMPLE 4

Preparation of Crystalline Polymorph Form II of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Approximately 1 g of crude starting material prepared as described in Example 1 was dissolved in refluxing acetone (10 mL). Water (3 mL) was added to this mixture while maintaining a reflux temperature. The resulting yellow solution was allowed to cool without agitation to room temperature. The solids that formed were collected by filtration and washed with acetone-water (1:1, about 5 ml). The product was then dried in an oven (45° C., 29 psi vacuum, 24 hours) to yield 0.63 g of white crystals.

EXAMPLE 5

Preparation of Crystalline Polymorph Form II of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Approximately 1 g of crude starting material prepared as described in Example 1 was dissolved in hot 5 ml methylene chloride and was allowed to dry slowly in a fume hood. A form II material was obtained together with some amorphous form.

EXAMPLE 6

Preparation of Crystalline Polymorph Form III of (−)-4-[4-[4-[4-[[(2R-cis)-5-(2,4-difluorophenyl)tetrahydro-5-(1H-1,2,4-triazol-1-ylmethyl)furan-3-yl]-methoxy]phenyl]-1-piperazinyl]phenyl-2,4-dihydro-2-[(S)-1-ethyl-2(S)-hydroxylpropyl]-3H-1,2,4-triazol-3-one Approximately 2 g g of crude starting material prepared as described in Example 1 was dissolved in hot 10 ml methanol. The resulting solution was allowed to cool without agitation to room temperature in a fume hood. The solids that formed were collected by filtration and dried in the fume hood.

What is claimed is:

1. A crystalline polymorph Form I of the compound represented by the formula I

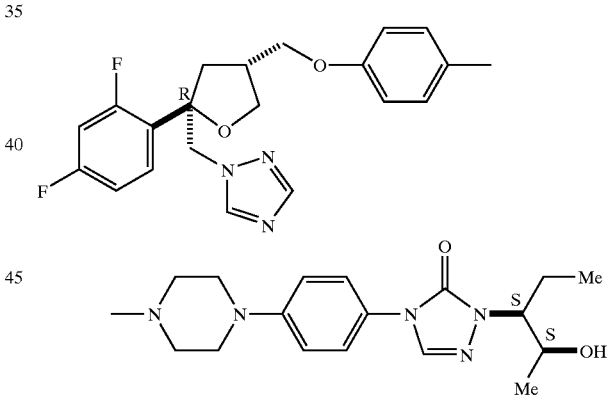

and characterized by at least one of the following properties:
- a melting point range of about 164 to about 165° C. wherein the melting point range is determined using USP Class Ia procedure;
- a specific rotation equal to $[\alpha]^{25}_D = -29.4°$ wherein the specific rotation is determined using a concentration of 10 mg/ml in methanol;
- an X-ray powder diffraction pattern substantially similar to that presented in FIG. 1;
- a differential scanning calorimetry thermogram substantially similar to that presented in FIG. 7; or
- the proton NMR spectrum substantially similar to that presented in FIG. 10.

2. A pharmaceutical composition comprising an antifungally effective amount of the crystalline polymorph form I of claim 1 and a pharmaceutically acceptable carrier.

3. A method of treating and/or preventing fungal infections in a mammal which comprises administering to said mammal an anti-fungally effective amount of the crystalline polymorph form I of claim 1.

4. A crystalline polymorph Form III of the compound represented by the formula I

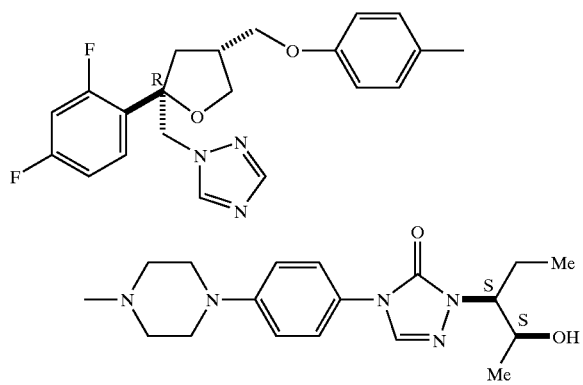

and characterized by an X-ray powder diffraction pattern displaying d spacing peaks at 28.69, 14.45, 10.59, 7.27, 6.59, 4.14, 3.58, and 3.53 +/−0.04.

5. The crystalline polymorph Form III of claim 4 further characterized by an X-ray powder diffraction pattern substantially similar to that presented in FIG. 3.

6. A pharmaceutical composition comprising an anti-fungally effective amount of the crystalline polymorph Form III of claim 4 and a pharmaceutically acceptable carrier.

7. A method of treating and/or preventing fungal infections in a mammal which comprises administering to said mammal an anti-fungally effective amount of the crystalline polymorph Form III of claim 4.

* * * * *

UNITED STATES PATENT AND TRADEMARK OFFICE
CERTIFICATE OF CORRECTION

PATENT NO. : 6,958,337 B2 Page 1 of 1
DATED : October 25, 2005
INVENTOR(S) : David R. Andrews et al.

It is certified that error appears in the above-identified patent and that said Letters Patent is hereby corrected as shown below:

<u>Column 14,</u>
Line 63, change "the" to -- a --.

Signed and Sealed this

Twenty-eighth Day of February, 2006

JON W. DUDAS
*Director of the United States Patent and Trademark Office*